United States Patent
Kashiwamura et al.

(10) Patent No.: US 6,730,626 B2
(45) Date of Patent: May 4, 2004

(54) TRANSITION METAL COMPOUNDS, POLYMERIZATION CATALYSTS FOR OLEFINS, OLEFIN POLYMERS AND PROCESS FOR THEIR PRODUCTION

(75) Inventors: Takashi Kashiwamura, Chiba (JP); Takuji Okamoto, Chiba (JP)

(73) Assignee: Idemitsu Petrochemical Co., Ltd., Tokyo (JP)

(*) Notice: Subject to any disclaimer, the term of this patent is extended or adjusted under 35 U.S.C. 154(b) by 0 days.

(21) Appl. No.: 10/130,306

(22) PCT Filed: Oct. 4, 2001

(86) PCT No.: PCT/JP01/08753
§ 371 (c)(1), (2), (4) Date: May 31, 2002

(87) PCT Pub. No.: WO02/28870
PCT Pub. Date: Apr. 11, 2002

(65) Prior Publication Data
US 2002/0193536 A1 Dec. 19, 2002

(30) Foreign Application Priority Data
Oct. 4, 2000 (JP) ......................................... 2000-306271

(51) Int. Cl.$^7$ ............................ B01J 31/38; C08F 4/44
(52) U.S. Cl. .................... 502/121; 502/122; 502/123; 502/155; 502/167; 526/161; 526/171
(58) Field of Search ................................ 526/161, 171, 526/172; 502/155, 167, 121, 122, 123

(56) References Cited

U.S. PATENT DOCUMENTS 6,339,135 B1   1/2002   Kashiwamura et al.

OTHER PUBLICATIONS

Sobota et al., Syntheses, Structure, and Reactivity of Chiral Titanium Compounds: Protocatalysts for Olefin Polymerization, Chem Eur. J. 2001, 7, No. 5, pp. 951–958.*

W.M. Coleman, III: "Ligand field effects on kinetic profiles in ethylene, alpha–olefin copolymerization" Appl. Catal., vol. 22, No. 2, pp. 345–359 1986.

Y. Abe et al.: "Titanium alkoxide to salicyl aldehyde oyobi 2–aminophenol no one–pot hannou ni yoru schiff base wo haiishi to suru titanium sakutai no ikusei kikou no kentou" Senryou to Yakuhin, vol. 39, No. 2, pp. 28–39 1994.

U.S. patent application Ser. No. 10/129,099, Kashiwamura et al., filed May 10, 2002.

U.S. patent application Ser. No. 10/130,306, Kashiwamura et al., filed May 31, 2002.

* cited by examiner

*Primary Examiner*—Robert Deshon Harlan
(74) *Attorney, Agent, or Firm*—Oblon, Spivak, McClelland, Maier & Neustadt, P.C.

(57) ABSTRACT

Useful as a catalyst component for polymerizing olefin is the transition metal compound of the present invention represented by Formula (I):

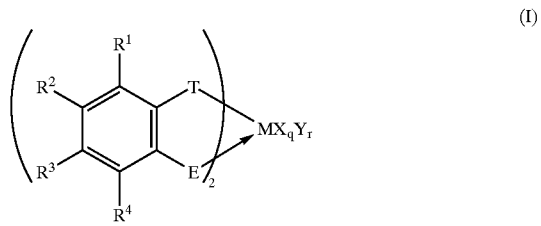

wherein M represents a transition metal compound of the fourth group in the periodic table; X represents a σ bonding ligand; Y represents a Lewis base; T represents a group containing a σ bonding atom; E is a specific group containing an atom which can coordinate with M via a lone pair; q is 1 or 2 and represents [(valency of M)–2]; r represents an integer of 0 to 3; $R^1$ to $R^4$ represent a hydrogen atom, a halogen atom, a hydrocarbon group, a halogen-containing hydrocarbon group, a silicon-containing group or a hetero atom-containing group.

10 Claims, No Drawings

TRANSITION METAL COMPOUNDS, POLYMERIZATION CATALYSTS FOR OLEFINS, OLEFIN POLYMERS AND PROCESS FOR THEIR PRODUCTION

BACKGROUND OF THE INVENTION

The present invention relates to a transition metal compound, a catalyst for polymerizing olefin, an olefin base polymer using the above catalyst and a production process for the same. More specifically, the present invention relates to a transition metal compound which is useful as a catalyst component for polymerizing olefin and which is easily synthesized, a highly active catalyst for polymerizing olefin which comprises the above transition metal compound and which efficiently provides olefin base homopolymers and copolymers, an olefin base polymer obtained by using this catalyst and a process for efficiently producing the same.

RELATED ART

As a catalyst for producing soluble polyolefin, a catalyst called a metallocene catalyst comprising a compound having a cyclopentadienyl ring as a ligand containing the fourth periodic table group transition metal have so far been known (Japanese Patent Application Laid-Open No. 19309/1983, Japanese Patent Application Laid-Open No. 217209/1985, Japanese Patent Application Laid-Open No. 167307/1990 and the like). These metallocene catalysts are characterized in that they provide polymers having a narrow molecular weight distribution and are excellent in a copolymerizing property, but they have the defect that complicated operation is necessary in synthesizing a metallocene compound and that the production cost inevitably comes higher.

On the other hand, as a novel catalyst which is different from them, the fourth periodic table group transition metal complexes of a non-metallocene base (Japanese Patent Application Laid-Open No. 315109/1999) and catalyst systems comprising various non-metallocene base transition metal complexes (Japanese Patent Application Laid-Open No. 227608/1992, Japanese Patent Application Laid-Open No. 203106/1986, Japanese Patent Application Laid-Open No. 115311/1991, International Patent Publication No. 99-12981 and International Patent Publication No. 98-27124) are developed in recent years. It is known that the non-metallocene base transition metal complexes described above are easily synthesized and provide catalysts for polymerizing olefins having a high activity.

However, catalysts systems comprising these non-metallocene base transition metal complexes are highly active to ethylene but have a very low activity in producing homopolymers and copolymers of α-olefins having 3 or more carbon atoms such as propylene, and they are not satisfactory from an industrial point of view.

DISCLOSURE OF THE INVENTION

Under such circumstances, an object of the present invention is to provide a novel transition metal compound which is useful as a catalyst component for polymerizing propylene and other α-olefins as well as ethylene and which is easily synthesized, a highly active catalyst for polymerizing olefins which comprises the above transition metal compound and which efficiently provides various olefin base homopolymers and copolymers, an olefin base polymer and copolymer obtained by using the above catalyst for polymerization. A further object of the present invention is to provide a production process for the same transition metal compound, catalyst, etc.

Intensive researches repeated by the present inventors in order to achieve the object of the present invention have resulted in finding that a transition metal compound having a specific structure is easily synthesized and useful as a catalyst component for polymerizing not only ethylene but also propylene and other α-olefins and that a catalyst for polymerization comprising the above transition metal compound and an activation cocatalyst has a high activity and efficiently provides ethylene (co)polymers, propylene (co)polymers and other olefin base (co)polymers. The present invention has been completed based on such knowledges.

That is, the present invention provides:

(1) a transition metal compound represented by Formula (I):

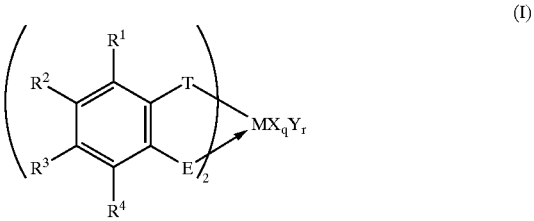

wherein M represents a transition metal element of the fourth group in the periodic table; X represents a σ bonding ligand which is bonded to M, and when plural X's are present, plural X's may be the same as or different from each other; Y represents a Lewis base, and when plural Y's are present, plural Y's may be the same as or different from each other; T represents a group containing a σ bonding atom which is bonded to M; E is a group containing an atom which can coordinate with M via a lone pair, and E represents $-OR^5$, $-SR^5$, $-SeR^5$, $-NR^5_2$, $-PR^5_2$ or $-P(O)R^5_2$; q is 1 or 2 and represents [(valency of M)−2]; r represents an integer of 0 to 3; $R^1$ to $R^4$ and $R^5$ each represent a hydrogen atom, a halogen atom, a hydrocarbon group having 1 to 20 carbon atoms, a halogen-containing hydrocarbon group having 1 to 20 carbon atoms, a silicon-containing group or a hetero atom-containing group; $R^1$ to $R^4$ may be the same as or different from each other and may form a ring together with an adjacent group; and when plural $R^5$'s are present, plural $R^5$'s may be the same as or different from each other, (2) a catalyst for polymerizing olefin, characterized by comprising the transition metal compound represented by Formula (I) and an activation-aid catalyst as principal components, (3) an olefin base polymer obtained by using the catalyst for polymerizing olefin described above, and (4) a production process for an olefin base polymer, characterized by homopolymerizing olefins or copolymerizing olefins with other olefins and/or other monomers in the presence of the catalyst for polymerizing olefin described above.

BEST MODE FOR CARRYING OUT THE INVENTION

The transition metal compound of the present invention is a novel compound represented by Formula (I):

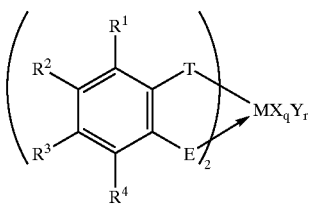

(I)

In Formula (I), M represents a transition metal element of the fourth group in the periodic table, and the specific examples thereof include titanium, zirconium and hafnium. Further in Formula (I), X represents a σ bonding ligand which is bonded to M, and when plural X's are present, plural X's may be the same as or different from each other. Said X includes a hydrogen atom, a halogen atom, a hydrocarbon group having 1 to 20 carbon atoms, an alkoxyl group having 1 to 20 carbon atoms, an aryloxy group having 6 to 20 carbon atoms, an amide group having 1 to 20 carbon atoms, a silicon-containing group having 1 to 30 carbon atoms, a phosphide group having 1 to 20 carbon atoms, a sulfide group having 1 to 20 carbon atoms and an acyl group having 1 to 20 carbon atoms. The halogen atom includes a chlorine atom, a fluorine atom, a bromine atom and an iodine atom. The hydrocarbon group having 1 to 20 carbon atoms includes, to be specific, alkyl groups such as methyl, ethyl, propyl, butyl, hexyl, cyclohexyl and octyl and alkenyl groups such as vinyl, propenyl and cyclohexenyl; arylalkyl groups such as benzyl, phenylethyl and phenylpropyl; and aryl groups such as phenyl tolyl, dimethylphenyl, trimethylphenyl, ethylphenyl, propylphenyl, biphenyl, naphthyl, methylnaphthyl, anthracenyl and phenanthryl. The alkoxyl group having 1 to 20 carbon atoms includes alkoxyl groups such as methoxy, ethoxy, propoxy and butoxy, phenylmethoxy and phenylethoxy. The aryloxy group having 6 to 20 carbon atoms includes phenoxy, methylphenoxy and dimethylphenoxy. The amide group having 1 to 20 carbon atoms includes alkylamide groups such as dimethylamide, diethylamide, dipropylamide, dibutylamide, dicyclohexylamide and methylethylamide; alkenylamide groups such as divinylamide, dipropenylamide and dicyclohexenylamide; arylalkylamide groups such as dibenzylamide, phenylethylamide and phenylpropylamide; and arylamide groups such as diphenylamide and dinaphthylamide. The silicon-containing group having 1 to 30 carbon atoms includes monohydrocarbon-substituted silyl groups such as methylsilyl and phenylsilyl; dihydrocarbon-substituted silyl groups such as dimethylsilyl and diphenylsilyl; trihydrocarbon-substituted silyl groups such as trimethylsilyl, triethylsilyl, tripropylsilyl, dimethyl (t-butyl) silyl, tricyclohexylsilyl, triphenylsilyl, dimethylphenylsilyl, methyldiphenylsilyl, tritolylsilyl and trinaphthylsilyl; hydrocarbon-substituted silyl ether groups such as trimethylsilyl ether; silicon-substituted alkyl groups such as trimethylsilylmethyl and phenyldimethylsilylethyl; silicon-substituted aryl groups such as trimethylsilylphenyl, and dimethylhydrosilyl and methyldihydrosilyl. The sulfide group having 1 to 20 carbon atoms includes alkylsulfide groups such as methylsulfide, ethylsulfide, propylsulfide, butylsulfide, hexylsulfide, cyclohexylsulfide and octylsulfide; alkenylsulfide groups such as vinylsulfide, propenylsulfide and cyclohexenylsulfide; arylalkylsulfide groups such as benzylsulfide, phenylethylsulfide and phenylpropylsulfide; and arylsulfide groups such as phenylsulfide, tolylsulfide, dimethylphenylsulfide, trimethylphenylsulfide, ethylphenylsulfide, propylphenylsulfide, biphenylsulfide, naphthylsulfide, methylnaphthylsulfide, anthracenylsulfide and phenanthrylsulfide.

The acyl group having 1 to 20 carbon atoms includes alkylacyl groups such as formyl, acetyl, propionyl, butylyl, valeryl, palmitoyl, stearoyl and oleoyl; arylacyl groups such as benzoyl, toluoyl, salyciloyl, cynnamoyl, naphthoyl and phthaloyl; and oxalyl, malonyl and succinyl which are derived from dicarboxylic acids such as oxalic acid, malonic acid and succinic acid.

Further in Formula (I), Y represents a Lewis base, and when plural Y's are present, they may be the same or different. Said Y includes amines, ethers, phosphines, thioethers, esters and nitriles. As the specific examples of Y, amines such as ammonia, methylamine, aniline, dimethylamine, diethylamine, N-methylaniline, diphenylamine, N, N-dimethylaniline, trimethylamine, triethylamine, tri-n-butylamine, methyldiphenylamine, pyridine and p-bromo-N, N-dimethylaniline, phosphines such as triethylphosphine, triphenylphosphine and diphenylphosphine, thioethers such as tetrahydrothiophene, esters such as ethyl benzoate and nitriles such as acetonitrile and benzonitrile can be described.

Furthermore in Formula (I), T represents a group containing a σ bonding atom which is bonded to M and includes, to be specific, $R^6{}_2C<$, $R^6{}_2Si<$, $R^6{}_2Ge<$, $R^6{}_2Sn<$, $R^6B<$, $R^6Al<$, $R^6P<$, $R^6N<$, oxygen (—O—), sulfur (—S—) and selenium (—Se—) (provided that $R^6$ is a hydrogen atom, a halogen atom, a hydrocarbon group having 1 to 20 carbon atoms, a halogen-containing hydrocarbon group having 1 to 20 carbon atoms, a silicon-containing group or a hetero atom-containing group, and when plural $R^6$'s are present, plural $R^6$'s may be the same as or different from each other). Among them, oxygen (—O—), sulfur (—S—) or selenium (—Se—), particularly oxygen is preferred in terms of easiness in synthesis and a yield.

Furthermore in Formula (I), E is a group containing an atom which can coordinate with M via a lone pair and represents —$OR^5$, —$SR^5$, —$SeR^5$, —$NR^5{}_2$, —$PR^5{}_2$ or —$P(O)R^5{}_2$ (provided that $R^5$ is a hydrogen atom, a halogen atom, a hydrocarbon group having 1 to 20 carbon atoms, a halogen-containing hydrocarbon group having 1 to 20 carbon atoms, a silicon-containing group or a hetero atom-containing group, and when plural $R^5$'s are present, plural $R^5$'s may be the same as or different from each other). Among them, —$NR^5{}_2$ or —$P(O)R^5{}_2$, particularly —$PR^5{}_2$ is preferred in terms of easiness in synthesis and a polymer yield.

Similarly in Formula (I), q is 1 or 2 and represents [(valency of M)–2], and r represents an integer of 0 to 3.

Moreover in Formula (I), $R^1$ to $R^4$ each represent a hydrogen atom, a halogen atom, a hydrocarbon group having 1 to 20 carbon atoms, a halogen-containing hydrocarbon group having 1 to 20 carbon atoms, a silicon-containing group or a hetero atom-containing group. These $R^1$ to $R^4$ may be the same as or different from each other and may form a ring together with an adjacent group.

In these $R^1$ to $R^4$ and $R^5$ and $R^6$ described above, the examples of the hydrocarbon group having 1 to 20 carbon atoms include alkyl groups such as methyl, ethyl, n-propyl, isopropyl, n-butyl, sec-butyl, tert-butyl, hexyl, cyclohexyl and octyl; alkenyl groups such as vinyl, propenyl and cyclohexenyl; arylalkyl groups such as benzyl, phenylethyl and phenylpropyl; and aryl groups such as phenyl tolyl, dimethylphenyl, trimethylphenyl, ethylphenyl, propylphenyl, biphenyl, naphthyl, methylnaphthyl, anthracenyl and phenanthryl.

The examples of the halogen-containing hydrocarbon group having 1 to 20 carbon atoms include p-fluorophenyl, 3,5-difluorophenyl, 3,4,5-trifluorophenyl, pentafluorophenyl, 3,5-bis (trifluoromethyl) phenyl and fluorobutyl. A silicon-containing group having 1 to 20 carbon atoms is preferred as the silicon-containing group and includes, to be specific, monohydrocarbon-substituted silyl groups such as methylsilyl and phenylsilyl; dihydrocarbon-substituted silyl groups such as dimethylsilyl and diphenylsilyl; trihydrocarbon-substituted silyl groups such as trimethylsilyl, triethylsilyl, tripropylsilyl, dimethyl (t-butyl) silyl, tricyclohexylsilyl, triphenylsilyl, dimethylphenylsilyl, methyldiphenylsilyl, tritolylsilyl and trinaphthylsilyl; hydrocarbon-substituted silyl ether groups such as trimethylsilyl ether; and silicon-substituted alkyl groups such as trimethylsilylmethyl and bis(trimethylsilyl) methyl.

Further, the examples of the hetero atom-containing group include methoxyethyl, diisopropylaminoethyl, furyl, methylfuryl, benzofuryl, methylthioethyl and thienyl.

Typical examples of the transition metal compound represented by Formula (I) described above are bis (2-diphenylphosphinophenoxy) zirconium dichloride, bis (2-dimethylphosphinophenoxy) zirconium dichloride, bis (2-diphenylphosphino-6-methylphenoxy) zirconium dichloride, bis (2-diphenylphosphino-6-isopropylphenoxy) zirconium dichloride, bis (2-diphenylphosphino-4-isopropylphenoxy) zirconium dichloride, bis (2-diphenylphosphino-6-tert-butylphenoxy) zirconium dichloride, bis (2-diphenylphosphino-4-tert-butylphenoxy) zirconium dichloride, bis(2-diphenylphosphino-4,6-di-tert-butylphenoxy)zirconium dichloride, bis(2-diphenylphosphino-4,6-diisopropylphenoxy)zirconium dichloride, bis(2-diphenylphosphino-4-methyl-6-tert-butylphenoxy)zirconium dichloride, bis(2-diphenylphosphino-4-tert-butyl-6-methylphenoxy)-zirconium dichloride, bis(2-dimethylaminophenoxy)-zirconium dichloride, bis(2-dimethylamino-6-methylphenoxy)zirconium dichloride, bis(2-dimethylamino-6-isopropylphenoxy)zirconium dichloride, bis(2-dimethylamino-4-isopropylphenoxy)zirconium dichloride, bis(2-dimethylamino-6-tert-butylphenoxy)-zirconium dichloride, bis(2-dimethylamino-4-tert-butylphenoxy)zirconium dichloride, bis(2-dimethylamino-4,6-di-tert-butylphenoxy)zirconium dichloride, bis(2-dimethylamino-4,6-diisopropylphenoxy)zirconium dichloride, bis(2-dimethylamino-4-methyl-6-tert-butylphenoxy)zirconium dichloride, bis(2-dimethylamino-4-tert-butyl-6-methylphenoxy)zirconium dichloride, bis(2-methoxyphenoxy)zirconium dichloride, bis(2-diphenylphosphino-6-trimethylsilylphenoxy)zirconium dichloride, bis(2-diphenylphosphinothiophenoxy)-zirconium dichloride, bis(2-diphenylphosphino-6-methylthiophenoxy)zirconium dichloride, bis(2-diphenylphosphino-6-iso-propylthiophenoxy)zirconium dichloride, bis(2-diphenylphosphino-6-tert-butylthiophenoxy)zirconium dichloride, bis(2-diphenylphosphino-4,6-di-tert-butylthiophenoxy)zirconium dichloride, bis(2-diphenylphosphino-4,6-di-iso-propylthiophenoxy)zirconium dichloride, bis(2-dimethylaminothiophenoxy)zirconium dichloride, bis(2-dimethylamino-6-iso-propylthiophenoxy)zirconium dichloride, bis(2-dimethylamino-6-tert-butylthiophenoxy) zirconium dichloride, bis(2-dimethylamino-4,6-di-tert-butylthiophenoxy)zirconium dichloride, bis(2-dimethylamino-4-methyl-6-tert-butylthiophenoxy) zirconium dichloride, bis(2-methoxythiophenoxy)zirconium dichloride, bis(2-diphenylphosphino-6-trimethylsilylthiophenoxy)-zirconium dichloride and compounds obtained by substituting zirconium contained in these compounds with titanium or hafnium. It is a matter of course that the examples shall not be restricted to these compounds.

The catalyst for polymerizing olefin according to the present invention comprises (A) the transition metal compound represented by Formula (I) described above and an activation cocatalyst as principal components. As the above activation cocatalyst, (B) a compound which can be reacted with the transition metal compound of the component (A) or a derivative thereof to form an ionic complex, or clay, clay mineral or an ion-exchangeable compound and (C) an organic aluminum compound used if necessary can be nominated.

Regarding the compound that can be reacted with the transition metal compound of the component (A) or the derivative thereof to form an ionic complex out of the components (B), (B-1) an ionic compound which is reacted with the transition metal compound of the component (A) to form an ionic complex, (B-2) aluminoxane, or (B-3) a Lewis acid can preferably be given from the viewpoint that the polymerization activity is high and the catalyst cost can be reduced.

Any compounds can be used as the (B-1) component as long as they are ionic compounds which are reacted with the transition metal compound of the component (A) to form ionic complexes, but particularly compounds represented by the following Formulas (II) and (III) are preferred from the viewpoint that polymerization active sites can efficiently be formed:

   (II)

   (III)

(Provided that $L^2$ is $M^1$, $R^8R^9M^2$, $R^{10}_3C$ or $R^{11}M^2$).

In Formulas (II) and (III), $L^1$ represents a Lewis base, and $[Z]^-$ represents a non-coordinative anion $[Z^1]^-$ or $[Z^2]^-$, in which $[Z^1]^-$ is an anion obtained by combining plural groups with an element, that is, $[M^3G^1G^2 \ldots G^f]$ (in which $M^3$ represents an element of the 5th to 15th group in the periodic table, preferably an element of the 13th to 15th group in the periodic table. In the above-description, $G^1$ to $G^f$ each represent a hydrogen atom, a halogen atom, an alkyl group having 1 to 20 carbon atoms, a dialkylamino group having 2 to 40 carbon atoms, an alkoxyl group having 1 to 20 carbon atoms, an aryl group having 6 to 20 carbon atoms, an aryloxy group having 6 to 20 carbon atoms, an alkylaryl group having 7 to 40 carbon atoms, an arylalkyl group having 7 to 40 carbon atoms, a halogen-substituted hydrocarbon group having 1 to 20 carbon atoms, an acyloxyl group having 1 to 20 carbon atoms, an organic metalloid group or a hetero atom-containing hydrocarbon group having 2 to 20 carbon atoms. Among $G^1$ to $G^f$, two or more groups may be combined to form a ring. Further in above description, f represents an integer of [(valency of the central metal $M^3$)+1]), $[Z^2]^-$ represents a Brœnsted acid alone in which a logarithm of an inverse number of an acid dissociation constant (pKa) is −10 or less or a conjugate base obtained by combining a Brönsted acid with a Lewis base or a conjugate base which is usually defined as a superacid, and it may be coordinated with a Lewis acid. Furthermore in the above description, $R^7$ represents a hydrogen atom, an alkyl group having 1 to 20 carbon atoms, an aryl group having 6 to 20 carbon atoms, an alkylaryl group or an arylalkyl group;

$R^8$ and $R^9$ each represent a cyclopentadienyl group, a substituted cyclopentadienyl group, a substituted indenyl group, a fluorenyl group or a substituted fluorenyl group; $R^{10}$ represents an alkyl group having 1 to 20 carbon atoms, an aryl group, an alkylaryl group or an arylalkyl group; $R^{11}$ represents a macrocyclic ligand such as tetraphenylporphyrin and phthalocyanine. Moreover in the above-description, h is an ionic valency of $[L^1—R^7]$ and $[L^2]$ and represents an integer of 1 to 3; a is an integer of 1 or more; b is (h×a); $M^1$ represents an element of the 1st to 3rd, 11th to 13th or 17th group in the periodic table; and $M^2$ represents an element of the 7th to 12th group in the periodic table.

In this respect, typical examples of $L^1$ are amines such as ammonia, methylamine, aniline, dimethylamine, diethylamine, N-methylaniline, diphenylamine, N,N-dimethylaniline, trimethylamine, triethylamine, tri-n-butylamine, methyldiphenylamine, pyridine, p-bromo-N,N-dimethylaniline and p-nitro-N,N-dimethylaniline, phosphines such as triethylphosphine, triphenylphosphine and diphenylphosphine, thioethers such as tetrahydrothiophene, esters such as ethyl benzoate and nitriles such as acetonitrile and benzonitrile.

Hydrogen, methyl, ethyl, benzyl and triethyl can be given as the specific examples of $R^7$, and cyclopentadienyl, methylcyclopentadieny, ethylcyclopentadienyl and pentamethylcyclopentadienyl can be given as the specific examples of $R^8$ and $R^9$. Phenyl, p-tolyl and p-methoxyphenyl can be given as the specific examples of $R^{10}$. Tetraphenylporphyrin, phthalocyanine and methallyl can be given as the specific examples of $R^{11}$. Also, Li, Na, K, Ag, Cu, Br and I can be given as the specific examples of $M^1$, and Mn, Fe, Co, Ni and Zn can be given as the specific examples of $M^2$.

Further, in $[Z^1]^-$, that is, $[M^3G^1G^2 \ldots G^f]$, B, Al, Si, P, As and Sb are preferred as the specific examples of $M^3$, and B or Al is preferred. The specific examples of $G^1$, $G^2$ to $G^f$ include the dialkylamino group such as dimethylamino and diethylamino; the alkoxyl group or aryloxy group such as methoxy, ethoxy, n-butoxy and phenoxy; the hydrocarbon group such as methyl, ethyl, n-propyl, isopropyl, n-butyl, isobutyl, n-octyl, n-eicosyl, phenyl, p-tolyl, benzyl, 4-t-butylphenyl and 3,5-dimethylphenyl; the halogen atom such as fluorine, chlorine, bromine and iodine; the hetero atom-containing hydrocarbon group such as p-fluorophenyl, 3,5-difluorophenyl, pentachlorophenyl, 3,4,5-trifluorophenyl, pentafluorophenyl, 3,5-bis(trifluoromethyl)phenyl and bis(trimethylsilyl)methyl; and the organic metalloid group such as pentamethylantimony, trimethylsilyl, trimethylgermyl, diphenylarsine, dicyclohexyantimony and diphenylboron.

Typical examples of the non-coordinative anion, that is, the Brönsted acid alone in which pKa is −10 or less or the conjugate base $[Z^2]^-$ obtained by combining a Brönsted acid with a Lewis acid are trifluoromethanesulfonic acid anion $(CF_3SO_3)^-$, bis(trifluoromethanesulfonyl) methyl anion, bis(trifluoromethanesulfonyl) benzyl anion, bis(trifluoromethanesulfonyl)amide, perchlorate anion $(ClO_4)^-$, trifluoroacetic acid anion $(CF_3CO_2)^-$, hexafluoroantimony anion $(SbF_6)^-$, fluorosulfonic acid anion $(FSO_3)^-$, chlorosulfonic acid anion $(ClSO_3)^-$, fluorosulfonic acid anion/antimony pentafluoride $(FSO_3/SbF_5)^-$, fluorosulfonic acid anion/arsenic pentafluoride $(FSO_3/AsF_5)$ and trifluoromethanesulfonic acid anion/antimony pentafluoride $(CF_3SO_3/SbF_5)^-$.

Typical examples of the ionic compound which is reacted with the transition metal compound of the component (A) described above to form the ionic complex, that is, the (B-1) component compound are triethylammonium tetraphenylborate, tri-n-butylammonium tetraphenyl-borate, trimethylammonium tetraphenylborate, tetraethylammonium tetraphenylborate, methyl (tri-n-butyl) ammonium tetraphenylborate, benzyl (tri-n-butyl) ammonium tetraphenylborate, dimethyldiphenyl-ammonium tetraphenylborate, triphenyl(methyl)ammonium tetraphenylborate, trimethylanilinium tetraphenyl-borate, methylpyridinium tetraphenylborate, benzylpyridinium tetraphenylborate, methyl(2-cyanopyridinium) tetraphenylborate, triethylammonium tetrakis (pentafluorophenyl)borate, tri-n-butylammonium tetrakis (pentafluorophenyl)borate, triphenylammonium tetrakis (pentafluorophenyl)borate, tetra-n-butylammonium tetrakis (pentafluorophenyl)-borate, tetraethylammonium tetrakis-(pentafluorophenyl)borate, benzyl(tri-n-butyl)ammonium tetrakis(pentafluorophenyl)borate, methyldiphenylammonium tetrakis(pentafluorophenyl)-borate, triphenyl(methyl) ammonium tetrakis-(pentafluorophenyl)borate, methylanilinium tetrakis-(pentafluorophenyl)borate, dimethylanilinium tetrakis(pentafluorophenyl)borate, trimethylanilinium tetrakis(pentafluorophenyl)borate, methylpyridinium tetrakis(pentafluorophenyl)borate, benzylpyridinium tetrakis(pentafluorophenyl)borate, methyl(2-cyanopyridinium) tetrakis(pentafluorophenyl)borate, benzyl (2-cyanopyridinium) tetrakis-(pentafluorophenyl)borate, methyl(4-cyanopyridinium) tetrakis(pentafluorophenyl) borate, triphenylphosphonium tetrakis(pentafluorophenyl)-borate, dimethylanilinium tetrakis[3,5-di(trifluoromethyl) phenyl]borate, ferrocenium tetraphenylborate, silver tetraphenylborate, trityl tetraphenylborate, tetraphenylporphyrinmanganese tetraphenylborate, ferrocenium tetrakis-(pentafluorophenyl)borate, (1,1'-dimethylferrocenium) tetrakis(pentafluorophenyl)borate, decamethyl-ferrocenium tetrakis(pentafluorophenyl)borate, silver tetrakis (pentafluorophenyl)borate, trityl tetrakis-(pentafluorophenyl)borate, lithium tetrakis-(pentafluorophenyl)borate, sodium tetrakis-(pentafluorophenyl)borate, tetraphenylporphyrin-manganese tetrakis(pentafluorophenyl)borate, silver tetrafluoroborate, silver hexafluorophosphate, silver hexafluoroarsenate, silver perchlorate, silver trifluoroacetate and silver trifluoromethanesulfonate.

The ionic compound reacted with the transition metal compound of said component (A) to form the ionic complex, which is the (B-1) component, may be used alone or in combination of two or more kinds thereof.

On the other hand, chain aluminoxane represented by the following Formula (IV) and cyclic aluminoxane represented by the following Formula (V) can be given as the aluminoxane of the (B-2) component:

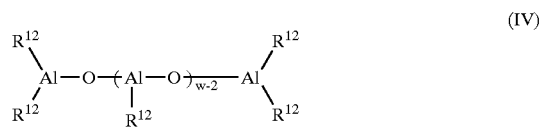

(IV)

(V)

wherein $R^{12}$'s each represent an alkyl group having 1 to 20 carbon atoms, preferably 1 to 8 carbon atoms, and they may be the same or different; w is an integer of $2 \leq w \leq 40$, and s is an integer of $1 < s \leq 50$.

To be specific, it includes aluminoxanes such as methylaluminoxane, ethylaluminoxane and isobutylaluminoxane.

A production process for the aluminoxane described above includes a process in which aluminum is brought into contact with a condensing agent such as water. However, the means therefor shall not specifically be restricted, and the reaction may be carried out according to a publicly known process. It includes, for example, a process in which an organic aluminum compound is dissolved in an organic solvent and in which this solution is brought into contact with water, a process in which an organic aluminum compound is added at first in polymerization and then water is added thereto, a process in which crystal water contained in a metal salt or water adsorbed on an inorganic matter and an organic matter is reacted with an organic aluminum compound and a process in which tetraalkyldialuminoxane is reacted with trialkylaluminum and further reacted with water. Aluminoxane that is insoluble in toluene may be used. The aluminoxane may be used alone or in combination of two or more kinds thereof.

The Lewis acid of the (B-3) component shall not specifically be restricted and may be either an organic compound or a solid inorganic compound. From the viewpoint that the active sites can efficiently be formed, boron compounds and aluminum compounds are preferably used as the organic compound, and magnesium compounds and aluminum compounds are preferably used as the inorganic compound. The above aluminum compounds include, for example, methyl bis (2,6-di-t-butyl-4-methylphenoxy) aluminum and methyl (1,1-bi-naphthoxy) aluminum; the magnesium compounds include, for example, magnesium chloride and diethoxymagnesium; the aluminum compounds include, for example, aluminum oxide and aluminum chloride; the boron compounds include, for example, triphenyl-boron, tris(pentafluorophenyl)boron, tris[3,5-bis (trifluoromethyl)phenyl]boron, tris[(4-fluoromethyl)phenyl]boron, trimethylboron, triethylboron, tri-n-butylboron, tris(fluoromethyl)-boron, tris(pentafluoroethyl)boron, tris(nanofluorobutyl)boron, tris(2,4,6-trifluorophenyl)boron, tris(3,5-difluorophenyl)boron, tris[3,5-bis(trifluorophenyl)]boron, bis(pentafluorophenyl)fluoroboron, diphenylfluoroboron, bis(pentafluorophenyl)chloroboron, dimethylfluoroboron, diethylfluoroboron, di-n-butylfluoroboron, pentafluorophenyldifluoroboron, phenyldifluoroboron, pentafluorophenyldichloroboron, methyldifluoroboron, ethyldifluoroboron and n-butyldifluoroboron.

These Lewis acids may be used alone or in combination of two or more kinds thereof.

On the other hand, in (B-4) the clay, clay mineral or ion-exchangeable compound out of the (B) components, clay is an aggregate of fine silicate hydrate minerals and is a substance which exhibits plasticity by mixing with a suitable amount of water and kneading and shows rigidity by drying and which is sintered by baking at a high temperature. The clay mineral is silicate hydrate that constitutes a principal component of clay. Either of the clay and the clay mineral may be used for the preparation of the olefin polymerization catalyst component described above, and they may be either natural substances or artificially synthesized substances.

An ion-exchangeable stratified compound is a compound having a crystalline structure in which planes constituted by ionic bond are parallel superposed on each other by a weak bonding power and in which ions contained therein are exchangeable. An ion-exchangeable stratified compound is included in the clay mineral.

To show the specific examples of these (B-4) components, for example, phyllosilicic acids can be given as the clay mineral. The phyllosilicic acids include phyllosilicic acid and phyllosilicate. As the phyllosilicate, natural compounds such as montmorillonite, saponite and hectolite which belong to a smectite group, illite and sericite which belong to a mica group and mixed layer minerals of a smectite group and a mica group or a mica group and a vermiculite group can be nominated. Further, tetrasilicon fluoride mica, laponite and smectone can be given as the synthetic compound. In addition to them, ionic crystalline compounds having a stratified crystalline structure which are not clay minerals, such as α-Zr(HPO$_4$)$_2$, γ-Zr(HPO$_4$)$_2$, α-Ti(HPO$_4$)$_2$ and γ-Ti(HPO$_4$)$_2$ can be employed.

Clays and clay minerals which do not belong to an ion-exchangeable stratified compound include clay which is called bentonite because of a low montmorillonite content, Kibushi clay in which a lot of other components are contained in montmorillonite, gairome clay, sepiolite showing a fibrous form, parigolskite, and amorphous or low crystalline allophane and imogolite.

Further, a particle having a volume average particle diameter of 10 μm or less is preferred as the (B-4) component, and a particle having a volume average particle diameter of 3 μm or less is more preferred. In general, particles have a particle diameter distribution, and the (B-4) content has preferably a particle diameter distribution in which a volume average particle diameter is 10 μm or less and the particles having a volume average particle diameter of 3.0 μm or less are contained in a proportion of 10% by weight or more, more preferably a particle diameter distribution in which a volume average particle diameter is 10 μm or less and the particles having a volume average particle diameter of 1.5 μm or less are contained in a proportion of 10% by weight or more. A method for measuring the volume average particle diameter and the contained proportion includes, for example, a measuring method using an equipment (CIS-1 manufactured by Galai Production Ltd.) for measuring a particle diameter by a light transmittance of a laser beam. Further, the (B-4) component may be subjected to acid treatment, alkali treatment, salts treatment or organic substance treatment. Particularly, the component that is pre-treated with an organic silicon compound and an organic aluminum compound is preferred since the polymerization activity is elevated.

Among these (B-4) components, the components having a high capability to adsorb quaternary ammonium salts or to react with clay to form an intercalation product (called intercalation) are preferable. The components shall not specifically be restricted and include quaternary alkyl ammonium salts, quaternary aryl ammonium salts, quaternary arylalkyl ammonium salts, quaternary benzyl ammonium salts, heteroaromatic ammonium salts and the like. For example, clay or clay mineral is preferred and, to be specific, philo-silicate is preferred. Further, smectite is preferred, and montmorillonite is particularly preferred. Tetrasilicon fluoride mica is preferred as a synthetic product.

A use proportion of the catalyst component (A) to the catalyst component (B) in the polymerizing catalyst of the present invention falls in a range of preferably 10:1 to 1:100, more preferably 2:1 to 1:10 in terms of a mole ratio when the (B-1) compound is used as the catalyst component (B). If it deviates from the range described above, the catalyst cost per a polymer unit weight grows high, and therefore it is not practical. Also, it falls in a range of preferably 1:1 to 1:1,000,000, more preferably 1:10 to 1:10,000 in terms of a mole ratio when the (B-2) compound is used. If it deviates from this range, the catalyst cost per a polymer unit weight grows high, and therefore it is not practical. A use proportion of the catalyst component (A) to the catalyst component (B-3) described above falls in a range of preferably 10:1 to 1:2,000, more preferably 5:1 to 1:1,000 and further preferably 2:1 to 1:500 in terms of a mole ratio. If it deviates from this range, the catalyst cost per a polymer unit weight goes up, and therefore it is not practical. In respect to a use proportion of the catalyst component (A) to the catalyst component (B-4), the transition metal complex of the component (A) falls in a range of 0.1 to 1,000 micromole, preferably 1 to 100 micromole per a unit weight [g] of clay of the component (B-4).

(B-1), (B-2), (B-3) and (B-4) can be used as the catalyst component (B-4) alone or in combination of two or more kinds thereof.

The polymerizing catalyst of the present invention may comprise the catalyst component (A) and the catalyst component (B) described above as principal components or may comprise the catalyst component (A), the catalyst component (B) and the organic aluminum compound (C) as principal components.

In this respect, used as the organic aluminum compound of the component (C) described above is a compound represented by Formula (VI):

$$R^{13}{}_v AlQ_{3-v} \qquad (VI)$$

wherein $R^{13}$ represents an alkyl group having 1 to 10 carbon atoms; Q represents a hydrogen atom, an alkoxyl group having 1 to 20 carbon atoms, an aryl group having 6 to 20 carbon atoms or a halogen atom; and v represents a real number of 1 to 3.

The specific examples of the compound represented by Formula (VI) include trimethylaluminum, triethylaluminum, triisopropylaluminum, triisobutylaluminum, dimethylaluminum chloride, diethylaluminum chloride, methylaluminum dichloride, ethylaluminum dichloride, dimethylaluminum fluoride, diisobutylaluminum hydride, diethylaluminum hydride and ethylaluminum sesquichloride. The trialkylaluminum compounds are preferred as this organic aluminum compound, and among them, trimethylaluminum and triisopropylaluminum are suited.

These organic aluminum compounds may be used alone or in combination of two or more kinds thereof.

A use proportion of the catalyst component (A) to the catalyst component (C) described above falls in a range of preferably 1:1 to 1:10,000, more preferably 1:5 to 1:2,000 and further preferably 1:10 to 1:1,000 in terms of a mole ratio. Use of the above catalyst component (C) makes it possible to elevate the polymerization activity per the transition metal, but if it is too much, particularly if it deviates from the range described above, the organic aluminum compound comes to nothing and remains in the polymer in a large amount. On the other hand, if it is small, the satisfactory catalyst activity is not obtained, and it is not preferred in a certain case.

In the present invention, among or after bringing the respective components into contact, the polymer such as polyethylene and polypropylene and the inorganic oxide such as silica and alumina may be allowed to coexist or brought into contact. In carrying them on a carrier, they are preferably carried on a polymer, and such carrier polymer has a particle diameter of usually 1 to 300 μm, preferably 10 to 200 μm and more preferably 20 to 100 μm. If this particle diameter is smaller than 1 μm, fine powders contained in the polymer are increased, and if it exceeds 300 μm, coarse particles contained in the polymer are increased and causes a reduction in the bulk density and clogging of a hopper in a manufacturing process. In this case, the carrier has a specific surface area of 1 to 1,000 m²/g, preferably 50 to 500 m²/g and a pore capacity of 0.1 to 5 m³/g, preferably 0.3 to 3 m³/g.

The contact may be carried out in hydrocarbon such as pentane, hexane, heptane, toluene and xylene in inert gas such as nitrogen. The addition or contact of the respective components not only can be carried out at a polymerizing temperature but also is preferably carried out at −30° C. to a boiling point of each solvent, particularly a room temperature to a boiling point of the solvent.

Such catalyst for polymerizing olefin according to the present invention makes it possible to homopolymerize or copolymerize not only ethylene but also propylene and other α-olefins at a high activity. Further, the transition metal compound that is the catalyst component (A) is easily synthesized, and the production cost of the catalyst is low.

The olefin base polymer of the present invention is obtained by using the catalyst for polymerizing olefin described above and can be produced by homopolymerizing olefins or copolymerizing olefins with other olefins and/or other monomers in the presence of the above catalyst for polymerizing olefin.

In the production process for the olefin polymer of the present invention, the organic aluminum compound (C) may be used by bringing in advance into contact with the component (A) and/or the component (B) or may be used by adding the component (C) to a reactor and then bringing into contact with the component (A) and the component (B). A use amount of the component (C) is the same as that of the catalyst for polymerizing olefin described above. According to the production process for the olefin polymer of the present invention, the homopolymerization of olefins or the copolymerization of olefins with other olefins and/or other monomers (that is, copolymerization of different kinds of olefins themselves, copolymerization of olefins with other monomers or copolymerization of different kinds of olefins with other monomers) in the presence of the polymerizing catalyst described above are suitably carried out.

The above olefins shall not specifically be restricted, and ethylene or α-olefin having 3 to 20 carbon atoms is preferred. This α-olefin includes, for example, α-olefins such as propylene, 1-butene, 1-pentene, 1-hexene, 1-heptene, 1-octene, 1-nonene, 1-decene, 4-phenyl-1-butene, 6-phenyl-1-hexene, 3-meyhyl-1-butene, 4-meyhyl-1-butene, 3-meyhyl-1-pentene, 4-meyhyl-1-hexene, 5-meyhyl-1-hexene, 3,3-dimeyhyl-1-pentene, 3,4-dimeyhyl-1-pentene, 4,4-dimeyhyl-1-pentene and vinylcyclohexane; halogen-substituted α-olefins such as hexafluoropropene, tetrafluoroethylene, 2-fluoropropene, fluoroethylene, 1,1-difluoroethylene, 3-fluoropropene, trifluoroethylene and 3,4-dichloroethylene; cyclic olefins such as cyclopentene, cyclohexene, norbornene, 5-methylnorbornene, 5-ethylnorbornene, 5-propylnorbornene, 5,6-dimethylnorbornene and 5-benzylnorbornene; styrenes including styrene and alkylstyrenes such as p-methylstyrene, p-ethylstyrene, p-propylstyrene, p-isopropylstyrene, p-butylstyrene, p-tert-butylstyrene, p-phenylstyrene, o-methylstyrene, o-ethylstyrene, o-propylstyrene, o-isopropylstyrene, m-methylstyrene, m-ethylstyrene, m-isopropylstyrene, m-butylstyrene, mesitylstyrene, 2,4-dimethylstyrene, 2,5-dimethylstyrene and 3,5-dimethylstyrene; alkoxystyrenes such as p-methoxystyrene, o-methoxystyrene and m-methoxystyrene; halogenated styrenes such as p-chlorostyrene, m-chlorostyrene, o-chlorostyrene, p-bromostyrene, m-bromostyrene, o-bromostyrene, p-fluorostyrene, m-fluorostyrene, o-fluorostyrene and o-methyl-p-fluorostyrene; trimethylsilylstyrene, vinyl benzoate and divinylbenzene. Those suitably selected from the olefins described above may be used for the other olefins.

In the present invention, the olefins described above may be used alone or in combination of two or more kinds thereof. In copolymerizing two or more kinds of olefins, the olefins described above can suitably be combined.

Further, in the present invention, the olefins described above may be copolymerized with other monomers, and capable of being given as the other monomers used in this case are, for example, chain diolefins such as butadiene, isoprene, 1,4-pentadiene and 1,5-hexadiene, polycyclic olefins such as norbornene, 1,4,5,8-dimethano-1,2,3,4,4a,5,8,8a-octahydronaphthalene and 2-norbornene, cyclic diolefins such as norbornadiene, 5-ethylidenenorbornene, 5-vinylnorbornene and dicyclopentadiene, and unsaturated esters such as ethyl acrylate and methyl methacrylate.

In the present invention, propylene is particularly suited as the olefins.

In the present invention, a process for polymerizing olefins shall not specifically be restricted, and capable of being employed are optional polymerizing methods such as a slurry polymerizing method, a solution polymerizing method, a gas phase polymerizing method, a bulk polymerizing method and a suspension polymerizing method.

When using a polymerization solvent, the solvent includes hydrocarbons and halogenated hydrocarbons such as benzene, toluene, xylene, n-hexane, n-heptane, cyclohexane, methylene chloride, chloroform, 1,2-dichloroethane and chlorobenzene. They may be used alone or in combination of two or more kinds thereof. Further, the monomers used for the polymerization can be used as well as the solvent depending on the kind thereof.

It is advantageous in terms of a polymerization activity and a reactor efficiency to select a use amount of the catalyst in the polymerization reaction so that that of the component (A) falls in a range of usually 0.5 to 100 micromole, preferably 2 to 25 micromole per liter of the solvent.

In respect to the polymerization condition, the pressure is selected in a range of usually an atmospheric pressure to 200 MPa·G. The polymerization temperature falls in a range of usually −50 to 250° C. A method for controlling a molecular weight of the polymer includes the kind and a use amount of the respective catalyst components, selection of the polymerization temperature and introduction of hydrogen. Further, in the polymerization of olefin in the present invention, the catalyst can be used to carry out pre-polymerization. Bringing a small amount of olefin into contact with the catalyst can carry out this pre-polymerization. In this case, the polymerization temperature is −20 to 100° C., preferably −10 to 70° C. and particularly preferably 0 to 50° C. Also, inert hydrocarbons, aliphatic hydrocarbons, aromatic hydrocarbons and monomers are used as a solvent used in this pre-polymerization. In particular, aliphatic hydrocarbons are preferred. This pre-polymerization can be carried out as well without using solvents. The pre-polymerization is preferably carried out so that the pre-polymerization product has a limiting viscosity [η] (measured in decalin at 135° C.) of 0.2 deciliter/g or more, preferably 0.5 deciliter/g or more, and the conditions are preferably controlled so that an amount of the pre-polymerization product is 1 to 10,000 g, preferably 10 to 1,000 g per millimole of the transition metal component contained in the catalyst.

The present invention shall be explained below in further details with reference to examples, but the present invention shall by no means be restricted by the following examples.

EXAMPLE 1

Synthesis of bis (2-diphenylphosphino-4,6-di-tert-butylphenoxy) zirconium dichloride In 150 ml of acetic acid, 20 g (96.9 millimole) of 2,4-di-tert-butylphenol was dissolved, and the solution was cooled on ice. Then, 5.0 ml (96.9 millimole) of bromine was added thereto drop by drop. After finishing dropwise addition, the temperature was elevated up to a room temperature, and the solution was stirred for 8 hours. Then, the reaction mixture was thrown into ice and water, and the aqueous layer was extracted with diethyl ether. The organic layer was dried on anhydrous magnesium sulfate, and then the solvent was distilled off under reduced pressure to obtain 19.96 g (yield: 72.0%) of 2-bromo-4, 6-di-tert-butylphenol.

Next, 5.0 g (17.5 millimole) of 2-bromo-4,6-di-tert-butylphenol described above was dissolved in 45 ml of dehydrated diethyl ether under nitrogen flow, and the solution was cooled down to −30° C. Then, 23.3 ml (37.3 millimole) of a hexane solution having an n-butyllithium concentration of 1.6 mole/liter was added thereto, and then the solution was stirred at a room temperature for 5 hours. The reaction mixture was cooled down to −30° C., and 3.26 ml (17.3 millimole) of diphenylchlorophosphine was added thereto and stirred at a room temperature for 8 hours. In this reaction solution, 2.6 ml (20.5 millimole) of trimethylsilyl chloride was added, and the solution was further stirred for 8 hours. Then, the solvent was distilled off under reduced pressure, and the residue was extracted with hexane. Subsequently, after the solvent was distilled off under reduced pressure, the residue was dissolved in hexane, and the solution was then cooled down to separate a precipitated solid matter, whereby 1.3 g (yield: 16%) of 4,6-di-tert-butyl-2-diphenylphosphinophenyl trimethylsilyl ether was obtained.

Next, 0.98 g (2.11 millimole) of this 4,6-di-tert-butyl-2-diphenylphosphinophenyl trimethylsilyl ether was dissolved in 15 ml of dehydrated tetrahydrofuran under nitrogen flow, and the solution was cooled down to −30° C. Then, a dehydrated tetrahydrofuran solution of 0.4 g (1.06 millimole) of a zirconium tetrachloride tetrahydrofuran adduct was added thereto step by step, and the solution was stirred at a room temperature for one hour. Further, the solution was refluxed for 3 days by heating. The solvent was distilled off under reduced pressure, and the residue was recrystallized from dichloromethane/hexane, whereby obtained was 0.29 g (yield: 29.0%) of bis (2-diphenylphosphino-4,6-di-tert-butylphenoxy) zirconium dichloride.

EXAMPLE 2

Polymerization of Ethylene

In a heated and dried autoclave of one liter 400 ml of toluene and 3 millimole of methylaluminoxane were added under nitrogen flow, and this mixture was heated up to 50° C. stirring at this temperature for 5 minutes. Then, 3 micromole of bis (2-diphenylphosphino-4,6-di-tert-butylphenoxy)-zirconium dichloride obtained in Example 1 was added thereto, and then ethylene was introduced thereinto to elevate the pressure up to 0.68 MPa. Polymerization was carried out in this state for 15 minutes.

After finishing the reaction, the reaction product was thrown into methanol to filter off a precipitated polymer, and the polymer was then washed with methanol, followed by heating and drying it under reduced pressure to thereby obtain 19.9 g of polyethylene.

This polyethylene had a melting point [Tm] of 135.6° C. and an intrinsic viscosity [η] (measured in decalin at 135° C.) of 3.17 deciliter/g.

The melting point [Tm] and the intrinsic viscosity [η] were measured by the following methods.

(1) Melting Point [Tm]

The temperature was elevated from 40° C. to 220° C. at 320° C./minute and maintained at 220° C. for 3 minutes, and then the temperature was lowered down to 0° C. at 10° C./minute and maintained at 0° C. for 3 minutes. Further, the temperature was elevated up to 220° C. at 10° C./minute, and a peak vertex in a melting peak in this procedure was designated as a melting point [Tm]. DSC7 manufactured by Perkin Elmer Co., Ltd. was used as the measuring instrument.

(2) Intrinsic Viscosity [η]

An automatic viscometer, model VMR-053 manufactured by Rigo Co., Ltd. was used to measure it in decalin at 135° C.

EXAMPLE 3

In a heated and dried autoclave of one liter 400 ml of toluene and 3 millimole of methylaluminoxane were added under nitrogen flow, and this mixture was heated up to 50° C. stirring at this temperature for 5 minutes. Then, 3 micromole of bis (2-diphenylphosphino-4,6-di-tert-butylphenoxy) zirconium dichloride obtained in Example 1 was added thereto, and then propylene was introduced thereinto to elevate the pressure up to 0.68 MPa. Polymerization was carried out in this state for one hour. After finishing the reaction, the reaction product was thrown into methanol to filter off a precipitated polymer, and the polymer was then washed with methanol, followed by heating and drying it under reduced pressure to thereby obtain 28.3 g of polypropylene.

This polymer had an intrinsic viscosity [η] (measured in decalin at 135° C.) of 0.20 deciliter/g.

COMPARATIVE EXAMPLE 1

Propylene was polymerized in the same manner as in Example 3, except that in Example 3, a complex having the following structure (described in Japanese Patent Application Laid-Open No. 315109/1999) was substituted for bis (2-diphenylphosphino-4,6-di-tert-butylphenoxy) zirconium dichloride:

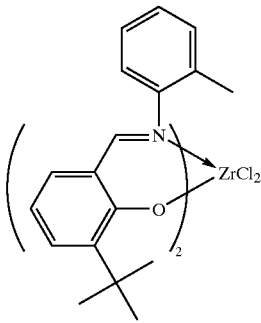

After finishing the reaction, the reaction product was thrown into methanol, but a solid matter was not obtained, and an organic solvent-soluble component was not obtained as well.

INDUSTRIAL APPLICABILITY

The transition metal compound of the present invention is useful as a catalyst component for polymerizing olefins and easily synthesized, and an olefin-polymerizing catalyst comprising this compound makes it possible to (co)polymerize not only ethylene but also propylene and other α-olefins at a high activity.

It is further understood by those skilled in the art that the foregoing description is a preferred embodiment of this invention and that various changes and modifications may be made in the invention without departing from the spirit and scope thereof.

What is claimed is:

1. A transition metal compound represented by Formula (I):

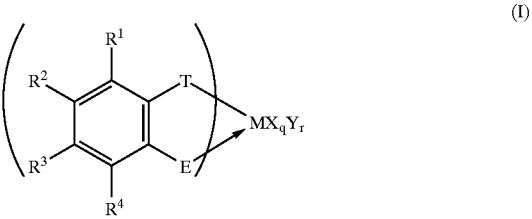

wherein M represents a transition metal compound of the fourth group in the periodic table; X represents a σ bonding ligand which is bonded to M, and when plural X's are present, plural X's may be the same as or different from each other; Y represents a Lewis base, and when plural Y's are present, plural Y's may be the same as or different from each other; T represents a group containing a σ bonding atom which is bonded to M; E is a group containing an atom which can coordinate with M via a lone pair and E represents —SR$^5$, —SeR$^5$, —NR$^5{}_2$, —PR$^5{}_2$ or —P(O)R$^5{}_2$; q is 1 or 2 and represents [(valency of M)–2]; r represents an integer of 0 to 3; R$^1$ to R$^4$ and R$^5$ each represent a hydrogen atom, a halogen atom, a hydrocarbon group having 1 to 20 carbon atoms, a halogen-containing hydrocarbon group having 1 to 20 carbon atoms, a silicon-containing group or a hetero atom-containing group; R$^1$ to R$^4$ may be the same as or different from each other and may form a ring together with an adjacent group; and when plural R$^5$'s are present, plural R$^5$'s may be the same as or different from each other.

2. The transition metal compound as described in claim 1, wherein T in Formula (I) is oxygen, sulfur or selenium.

3. The transition metal compound as described in claim 1, wherein T in Formula (I) is oxygen.

4. The transition metal compound as described in claim 1, wherein E in Formula (I) is —NR$^5{}_2$ or —PR$^5{}_2$.

5. The transition metal compound as described in claim 1, wherein E in Formula (I) is —PR$^5{}_2$.

6. A catalyst for polymerizing olefin, comprising a transition metal compound represented by Formula (I):

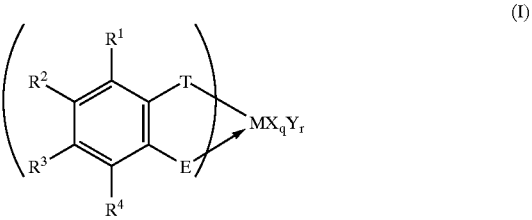

wherein M represents a transition metal compound of the fourth group in the periodic table; X represents a σ bonding ligand which is bonded to M, and when plural X's are present, plural X's may be the same as or different from each other; Y represents a Lewis base, and when plural Y's are present, plural Y's may be the same as or different from each other; T represents a group containing a σ bonding atom which is bonded to M; E is a group containing an atom which can coordinate with M via a lone pair and E represents —$SR^5$, —$SeR^5$, —$NR^5_2$, —$PR^5_2$ or —$P(O)R^5_2$; q is 1 or 2 and represents [(valency of M)–2]; r represents an integer of 0 to 3; $R^1$ to $R^4$ and $R^5$ each represent a hydrogen atom, a halogen atom, a hydrocarbon group having 1 to 20 carbon atoms, a halogen-containing hydrocarbon group having 1 to 20 carbon atoms, a silicon-containing group or a hetero atom-containing group; $R^1$ to $R^4$ may be the same as or different from each other and may form a ring together with an adjacent group; and when plural $R^5$'s are present, plural $R^5$'s may be the same as or different from each other;

and an activation cocatalyst as principal components.

7. The catalyst for polymerizing olefin as described in claim 6, wherein said activation cocatalyst is a compound that can be reacted with the transition metal compound as described in Formula (I) or a derivative thereof to form an ionic complex, or wherein said activation cocatalyst is clay, clay mineral or an ion-exchangeable compound.

8. The catalyst for polymerizing olefin as described in claim 6, wherein said activation cocatalyst is a combination of a compound that can be reacted with the transition metal compound as described in Formula (I) or a derivative thereof to form an ionic complex, or wherein said activation cocatalyst is clay, clay mineral or an ion-exchangeable compound and an organic aluminum compound.

9. An olefin base polymer obtained by polymerizing olefin in the presence of the catalyst as described in claim 6.

10. A production process for an olefin base polymer, comprising homopolymerizing olefins or copolymerizing olefins with other olefins and/or other monomers in the presence of said catalyst as described in claim 6.

* * * * *

UNITED STATES PATENT AND TRADEMARK OFFICE
CERTIFICATE OF CORRECTION

PATENT NO. : 6,730,626 B2
DATED : May 4, 2004
INVENTOR(S) : Kashiwamura et al.

It is certified that error appears in the above-identified patent and that said Letters Patent is hereby corrected as shown below:

<u>Title page,</u>
Item [30], should read:
-- [30]   Foreign Application Priority Data
     Oct. 5, 2000 (JP)………………… 2000-306271 --

Signed and Sealed this

Sixth Day of July, 2004

JON W. DUDAS
*Acting Director of the United States Patent and Trademark Office*